United States Patent [19]
Rast et al.

[11] Patent Number: 5,419,116
[45] Date of Patent: May 30, 1995

[54] MINISCALE BALLISTIC MOTOR TESTING METHOD FOR ROCKET PROPELLANTS

[75] Inventors: Robert H. Rast, Nanjemoy; Sharon M. Boyles; Phyllis E. Obney, both of Indian Head, all of Md.

[73] Assignee: The United States of America as represented by the Secretary of the Navy, Washington, D.C.

[21] Appl. No.: 213,283

[22] Filed: Mar. 15, 1994

Related U.S. Application Data

[63] Continuation of Ser. No. 86,404, Jul. 2, 1993, abandoned.

[51] Int. Cl.$^6$ ............................................. G01L 3/26
[52] U.S. Cl. .............................. 60/204; 60/253; 73/116
[58] Field of Search ................. 60/204, 253, 39.33; 73/116, 117.1, 117.2, 117.3, 117.4

[56] References Cited

U.S. PATENT DOCUMENTS

| | | | |
|---|---|---|---|
| 3,015,231 | 1/1962 | Ganahl | 73/117.1 |
| 4,409,821 | 10/1983 | Battles et al. | 73/116 |
| 4,554,823 | 11/1985 | Lilley | 73/116 |

*Primary Examiner*—Richard A. Bertsch
*Assistant Examiner*—William Wicker
*Attorney, Agent, or Firm*—Jacob Shuster

[57] ABSTRACT

A method for using a miniscale ballistic test motor for determining burn rates over an operating pressure range allows the testing of a small propellant sample. The small propellant sample allows performance of an abbreviated procedure for each test of the propellant sample involving loading of a small scale test motor with the sample, conditioning the test motor and sample therein, firing the propellant sample and recording data.

13 Claims, 3 Drawing Sheets

MINISCALE BALLISTIC MOTOR TESTING METHOD FOR ROCKET PROPELLANTS

CROSS-REFERENCES TO RELATED APPLICATIONS

The present invention relates generally to the testing of rocket propellant and in particular to small scale rocket motor testing, as disclosed in prior application Ser. No. 08/086,404, filed Jul. 2, 1993, now abandoned, with respect to which this application is a continuation.

BACKGROUND OF THE INVENTION

Solid rocket propellant must be designed, evaluated and produced so as to evolve or generate hot gas in a controllable manner. This controlled evolvement of hot gas can then be utilized to propel a missile, rocket or other projectile in a predictable way.

It is well known to those skilled in the art that to ensure controlled gas evolution (burning), the following ballistic performance parameters of the propellant must be measured:

(1) burn rate (r) as a function of pressure, generally given by (r) in the equation $r = aP^n$, where P is the pressure;

(2) burn rate exponent, generally given by (n) in the same equation;

(3) burn rate pre-factor, generally given by (a) in the same equation;

(4) burn rate sensitivity to temperature given by $$\frac{1}{r}\left(\frac{\partial r}{\partial T}\right)_p$$

written as $\sigma_p$; and (5) pressure sensitivity with respect to area ratio where the area ratio is defined as K=propellant burning surface area divided by rocket nozzle throat area, where the pressure sensitivity is defined as:

$$\pi_k = \frac{1}{p}\left(\frac{\partial p}{\partial r}\right)_k$$

There are two methods presently used to measure the foregoing quantities. The first is called strand burning. Well-known to those skilled in the art is the *Chemical Propulsion Information Agency*(CPIA) handbook which contains standard data for strand burning of various propellants, some of which data is contained in graph form. This method consists of cutting the propellant into spaghetti size strands and then burning them at various constant temperatures and pressures. The strands must be burned in a costly device, a Crawford Bomb, which requires much maintenance. Additionally, many strands must be burned (requiring multiple test burns) to collect the data required to evaluate the aforementioned parameters (1) through (4). This procedure is very time consuming and expensive. Parameter (5) cannot be evaluated by the strand burning method.

Further, the foregoing known strand burning method does not allow testing of the propellant under the actual conditions inside a rocket motor. Although the strands are brought to the required pressure by external means, such as nitrogen pressure, and then ignited and burned, such environment does not simulate the turbulent conditions the propellant actually experiences inside a rocket motor.

The second known method uses a Ballistic Evaluation Motor (BEM). Such method has two advantages over strand burning. First, the BEM allows evaluation of all five parameters, not just (1) through (4). Secondly, the propellant can be evaluated in an environment that simulates conditions inside a rocket motor. Such simulation is not possible with strand burning.

There are several types of BEM's used by those familiar with propellant evolution technology. All types share the same disadvantages. They are expensive, time consuming to use and as in strand burning, they require large quantities of propellant.

There are many circumstances where large quantities of propellant are not available to test. These include:

(a) research and development programs where small (one to two gallon) quantities of new experimental propellants are formulated;

(b) lot set evaluations where new lots of propellant ingredients are evaluated by making small (less than five gallons) mixes; and (c) surveillance programs where small (less than five inches in diameter) missiles are dismantled and propellant grain is removed for testing. In each of these situations there is insufficient propellant to test completely by the prior art methods described.

SUMMARY OF THE INVENTION

It is therefore an object of the invention to provide an improved test for rocket propellant to determine ballistic performance parameters.

It is another object of the invention to test rocket propellant under conditions simulating the turbulence and pressure environment of a full scale rocket motor.

A further object is to produce valid test data (matching actual scale test results) while using small propellant charges (sizes between 2 and 5 ounces).

Accordingly, the invention involves a miniscale ballistic test motor, having a multi-pan assemblable body unit, which can be charged and then heated or cooled to operation temperatures prior to firing in order to simulate the environment within a full scale rocket motor. The test motor comprises a metal cylindrical body threaded on each end. A smaller concentric inert liner is fired inside the cylindrical body and washer-shaped insulator caps are inserted into each end. Forward and aft caps are screwed onto the cylindrical body to hold the insulator and inert liner in place and seal the burning chamber. A nozzle is attached using a threaded retainer engaging the threaded end of the aft cap. The replaceable insulators and liner are reusable depending on their condition. Typically six to eight test runs can be accomplished on each set of insulators and liners. The nozzle is also reusable. However, each test typically requires a specifically-sized nozzle. The entire assembly is sealed with o-ring seals. The testing sequence includes the following steps: preparing a small size slab of propellant, typically by die cutting to produce approximately a 2.5"×1.75" slab; loading the prepared slab along with igniters into the miniscale ballistic test motor; conditioning the motor and propellant assembly by heating in an oven to the desired test temperature; mounting the conditioned assembly on a test stand and attaching instrumentation; firing the motor and; recording test data.

BRIEF DESCRIPTION OF THE DRAWING FIGURES

The foregoing objects and other advantages of the present invention will be more fully understood from the following detailed description and reference to the appended drawings wherein.

DETAILED DESCRIPTION OF THE INVENTION

Figure 1:
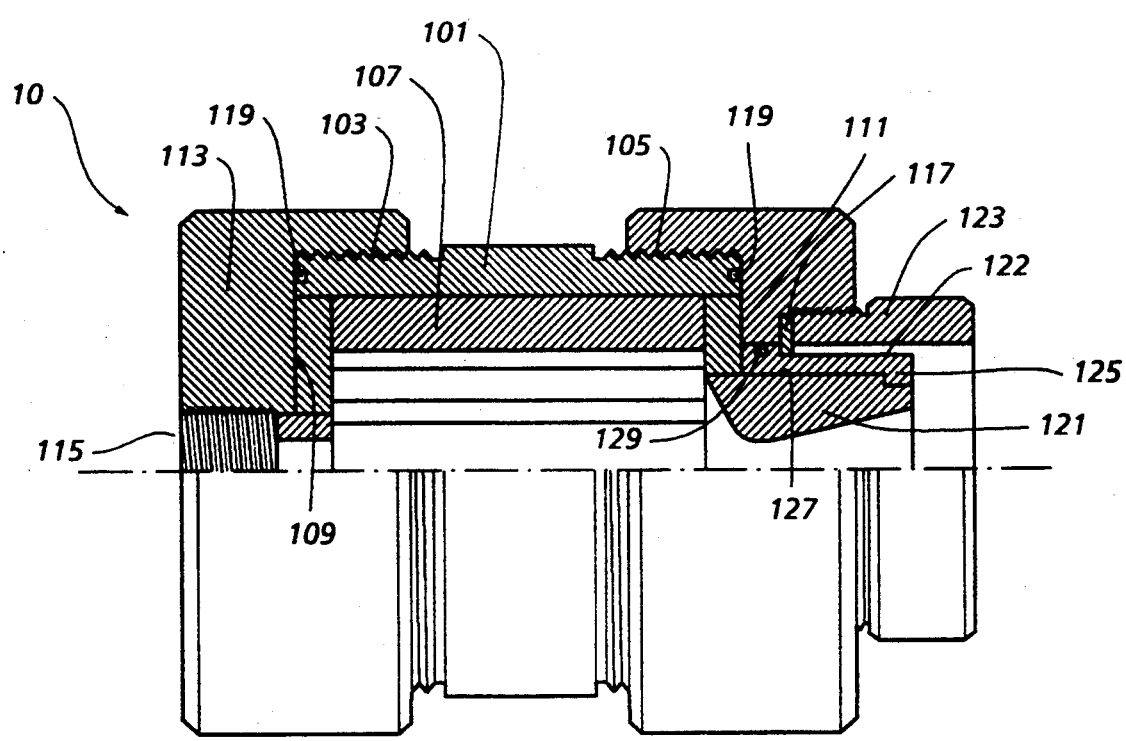
FIG. 1 is a partial cross-sectional view of the miniscale ballistic test motor.

Referring now to FIG. 1, the miniscale ballistic test motor generally referred to by reference numeral 10, is shown with its major components. The test motor 10 comprises a cylindrical metal body 101 having a threaded forward end 103 and a threaded aft end 105 between which a burning chamber is sealed as hereinafter described. In the preferred embodiment, cylindrical metal body 101 is constructed of a hardened tool steel. Assembly of test motor 10 is accomplished by sliding a cylindrical inert liner 107 for the chamber inside metal body 101. In the preferred embodiment the inert liner is made of phenolic fiberglass material. The cylindrical inert liner 107 is shorter than metal body 101, thereby forming a recess at each end. At the forward end insulator 109 is seated while at the aft end insulator 111 is seated. Inert liner 107 is cylindrical in shape. Forward end insulator 109 is disk-shaped having an opening in the center to provide access for instrumentation. Aft end insulator 111 is also disk-shaped having a larger opening in its center to provide for an exhaust port. Forward end cap 113 is screwed onto the threaded forward end 103 of metal body 101. Forward end cap 113 has a threaded opening 115 which is aligned with the opening in insulator 109 and permits attachment of a transducer to measure pressure within the test motor chamber. Aft end cap 117 screws onto the threaded aft end 105 of threaded forward end 103 retaining aft insulator 111 in a similar manner. Both end caps are sealed by o-rings 119 on each end of the threaded forward end 103. Aft end cap 117 has a threaded opening in its center to provide a means of securing a nozzle assembly which comprises an exhaust nozzle 121, a nozzle shell 122, and a nozzle retainer 123. In the preferred embodiment, exhaust nozzle 121 is constructed of an ablative composite material, such as a carbon composite. Exhaust nozzle shell 121, after being machined to a pre-determined size, is slid into the nozzle shell 122. The assembly having a friction-tight fit in addition to a retaining interior shoulder 125 on the nozzle shell, maintains the nozzle in position. An exterior shoulder 127 on the nozzle shell provides a surface of nozzle retainer 123 to secure the assembly against the aft insulator 111. An o-ring 129 is also provided between aft end cap 117 and nozzle shell 122, thereby completing the sealing of the chamber of the mini-motor.

Internal ballistics (and sizing of the exhaust nozzle) are calculated on the assumptions that: a) Nozzle flow is one dimensional and isentropic; b) Propellant regresses equally, normally on all slab faces; c) Nozzle throat area remains constant or changes linearly with time; and d) The perfect gas law applies to combustion products.

The mass flow through the nozzle is determined by:

$$m_n = \frac{PA_t}{C^*}$$

where $m_n$ is the nozzle mass flow, P is chamber pressure and $A_t$ is the nozzle throat area. $C^*$ is the characteristic velocity. Coupled with the known geometry of the sample, this equation is integrated to give the burn rate as a function of pressure, as follows:

$$\Delta m_T = \frac{1}{C^*} \int_{t_A}^{t_D} PA_t dt$$

Figure 2:
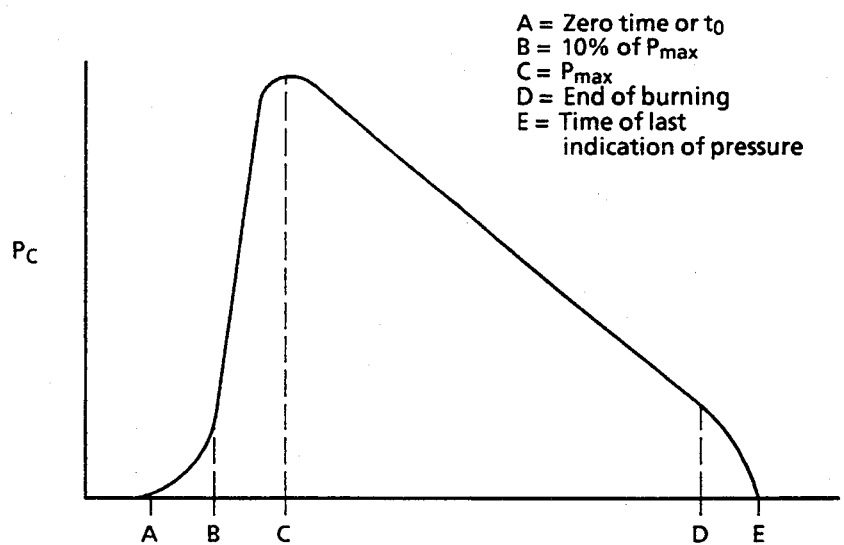
FIG. 2 is a chart showing Pressure vs Time nomenclature during motor firing.

When the foregoing is integrated to where $t_A$ and $t_p$ are as shown in FIG. 2, $\Delta m_T$ is the total mass flow through the nozzle.

$C^*$ is assumed constant over the entire pressure range. Mass flow from $t_A$ to any time t is determined by:

$$\Delta m_T = \frac{1}{C^*} \int_{t_A}^{t} PA_t dt$$

The portion of mass at any time t is determined by dividing the total mass flow to time t by total mass flow $$\frac{\Delta m_t}{\Delta m_T} = \frac{\int_{t_A}^{t} PA_t dt}{\int_{t_A}^{t_D} PA_t dt}, \text{ where}$$

where
$\Delta m_t$ = mass of propellant burned from time $t_A$ to time t and $\Delta m_T$ = original mass of propellant $M_o$ (neglecting any residue). Using $m_p = p_p V_p$, where $p_p$ and $V_c$ are propellant density and volume, then $$\frac{\Delta v_t}{V_o} = \frac{\int_{t_A}^{t} PA_t dt}{\int_{t_A}^{t_f} PA_t dt}$$

where $V_o$ is the original propellant volume.

Since $V_o$, P, t and $A_t$ are measured quantities and the geometry of the sample is known, the distance $\delta t$ can be calculated as $$r_{avg} = \frac{\delta x}{\delta t}, \text{ where}$$

$r_{avg}$ is the average burn rate over internal $\delta t$ corresponding to average pressure for the time interval given by $$P_{avg} = \frac{\int Pdt}{\delta t}.$$

Referring now to FIG. 2, The Pressure vs. Time nomenclature is depicted as typically plotted from data produced by mini-motor test firings. Firing is initiated at time zero ($t_0$) identified by point 'A' with burning beginning on the left side of the figure and ending on the right side of the figure. After initiation, pressure builds to ten (10) percent of maximum ($P_{max}$) as identified over by point 'B'. At point 'C' combustion chamber pressure ($P_{max}$) is reached and thereafter a continuous test burn occurs with generally decreasing pressure to burn out at point 'D'. The residual pressure is released by 'E'.

Figure 3:
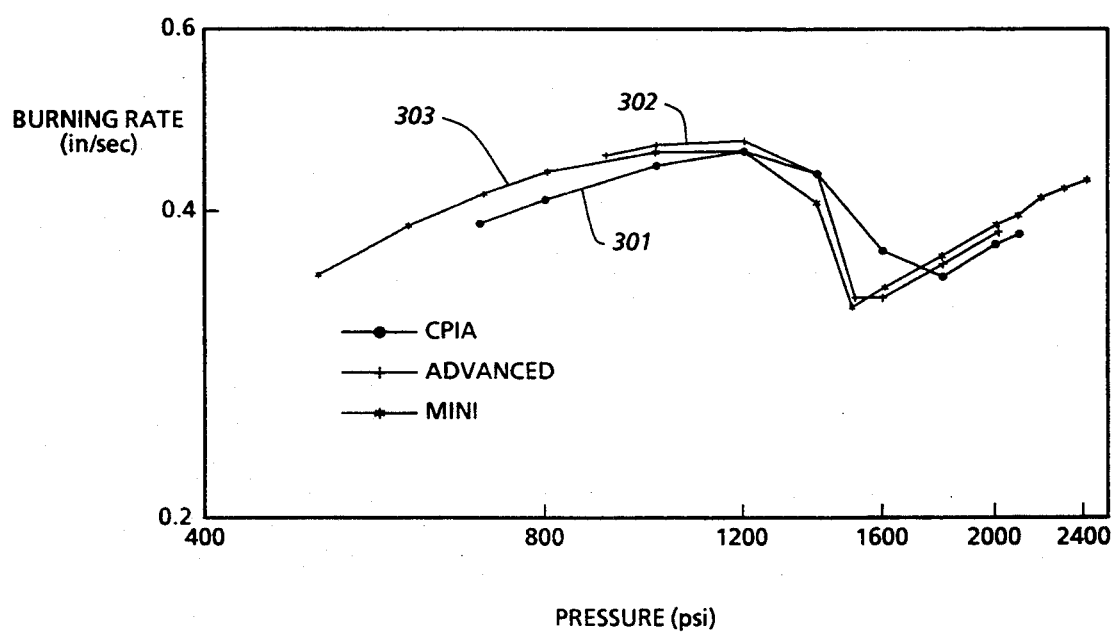
FIG. 3 is a chart comparing performance of the miniscale motor with a standard and an advanced slab motor at 40° F.
Figure 4:
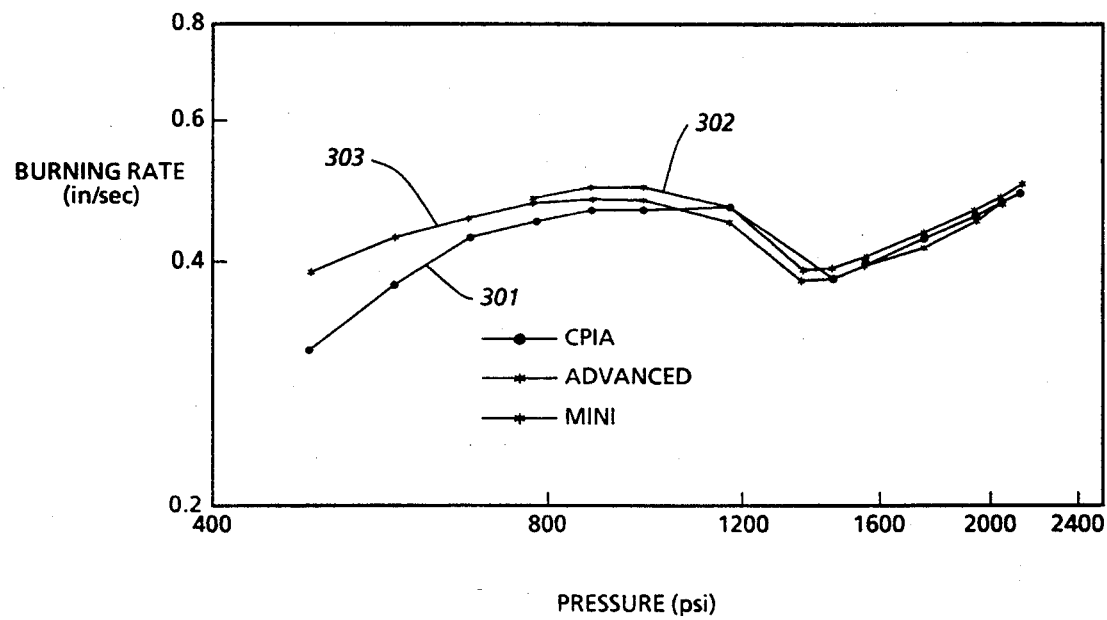
FIG. 4 is a chart comparing performance of the miniscale motor with a standard and an advanced slab motor at 70° F.
Figure 5:
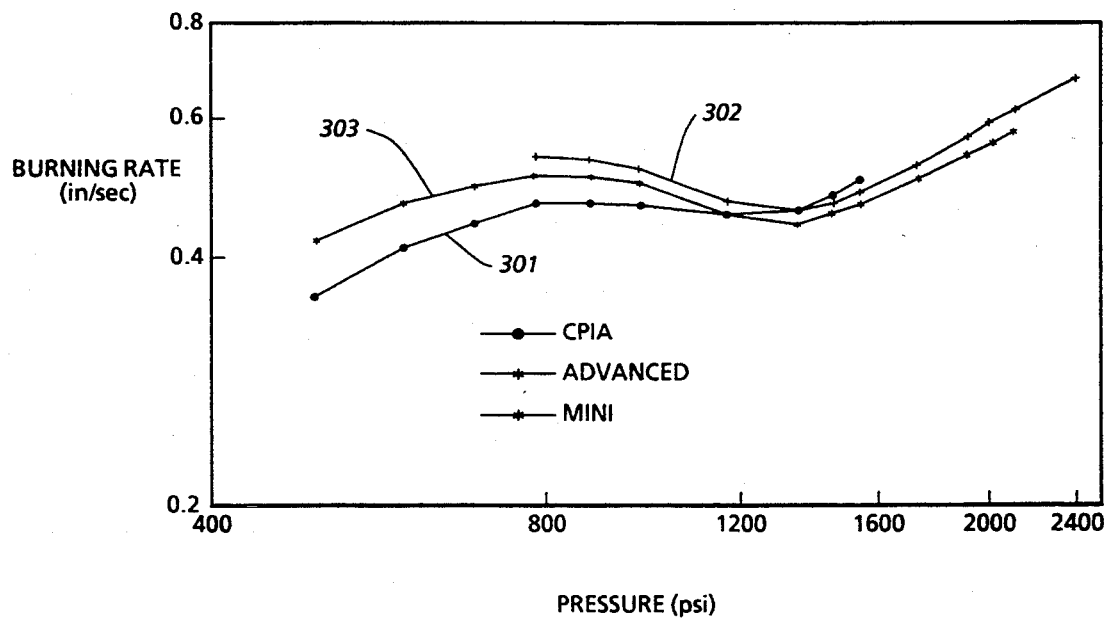
FIG. 5 is a chart comparing performance of the miniscale motor with a standard and advanced slab motor, at 165° F.

A comparison of the standard *Chemical Propulsion Information Agency*(CPIA) handbook data for various temperatures is shown in FIGS. 3 through 5. Burning as reflected on the charts of these figures proceeds from right to left (the opposite of FIG. 2 since pressure vs. burn rate is shown). As can be seen, the standard data 301 (CPIA handbook) has a small non-correlation with the advanced (experimental) data 302 except at certain pressures. The mini-motor data 303 provides a much higher degree of correlation at all pressure levels including the reduction in burn rate over the 1800 to 1500 psi region. The pressure-burn rate anomaly depicted in FIGS. 3–5 is a characteristic of N-5 propellant well known in the art but poorly defined by CPIA strand burning data. A Comparison of the three charts, FIGS. 3–5, shows the same high degree of optimized correlation between the mini-motor database 303 and the advanced data 302 for temperatures of −40° F., 70° F. and 165° F.

Preparation of slab of propellant can be accomplished by using a die-cutter since the sample size of the mini-motor is much smaller than the conventional advanced test motor. Of course the conventional method of machining a test slab of propellant may also be used. Typically the slab size is only two to three ounces. After preparation, a pre-selected charge of a propellant is loaded into the miniscale test motor, which is then conditioned by heating or cooling to a selected operating temperature at which burn rate correlation is optimized at all pressure levels as aforementioned. The conditioned and charged miniscale test motor is then positioned in a firing fixture and instrumentation is attached for pressure reading and recording. The miniscale test motor is then fired and test data is recorded. The advantages and benefits of miniscale ballistic test motor are numerous. The hardware is inexpensive and not easily damaged because of the smaller, more rugged size and robust design. Further, individual parts can easily be machined locally if required. Additionally, the mini-motor provides better correlation to the advanced test motor than the standard (CPIA) data and much better correlation than results obtained from individual strand burning. Also the smaller propellant sample required allows die-cutting (as opposed to the machining normally required) and allows preparation of a test sample from a small batch, typically 1–2 gallons.

Although the invention has been described relative to a specific embodiment thereof, there are numerous variations and modifications that will be readily apparent to those skilled in the art in the light of the above teachings. It is therefore to be understood that, within the scope of appended claims, the invention may be practiced other than as specifically described.

What is claimed as new and desired to be secured by Letters Patent of the United States is:

1. A method for testing propellant of a rocket, comprising the steps of:
   a) preparing said propellant by reduction in size thereof to a preselected slab;
   b) loading said pre-selected slab of the propellant into a chamber;
   c) conditioning the chamber loaded with the propellant by heating to a selected test temperature;
   d) attaching instrumentation to the conditioned chamber for measurement of environment therein;
   e) firing the preselected slab of the propellant within the loaded chamber; and
   f) recording test data from the instrumentation resulting from said firing of the propellant within the chamber.

2. A method for testing the propellant as in claim 1, wherein said step of preparing the propellant comprises die-cutting a sample of the propellant reduced to a weight approximately three ounces.

3. A method for testing the propellant as in claim 1, wherein said step of preparing the propellant comprises machining a sample of the propellant into said preselected.

4. The method of claim 1 wherein the test data obtained by said step of recording from the instrumentation relates to burn rate of the propellant and pressure produced during said firing thereof.

5. The method of claim 1 wherein said chamber is of a reduced size compared to a full scale chamber in the rocket.

6. The method of claim 1 wherein said step of conditioning the chamber includes simulation of ballistic turbulence and pressure internally within a full scale rocket motor as the environment is measured within the chamber by the instrumentation.

7. The method of claim 4 wherein the test data obtained by said step of recording from the instrumentation relates to burn rate of the propellant and pressure produced during said firing thereof.

8. The method of claim 1 wherein said chamber is formed in a miniscale ballistic rocket motor within which simulated turbulence and pressure is effected by said step of conditioning.

9. The method of claim 6 wherein the test data obtained by said step of recording from the instrumentation relates to burn rate of the propellant and pressure produced during said firing thereof.

10. In a method of testing propellant utilized in a full scale rocket motor by burning thereof within a chamber of a subscale rocket motor to obtain test data therefrom, the steps of: preparing the propellant by extraction of a sample therefrom between two and three ounces in weight; loading said sample into the chamber; and establishing conditions for the sample within the chamber before burning of the propellant including heating of the sample within the chamber to a selected temperature to simulate turbulence and pressure environment within the full scale rocket motor.

11. In a method of testing a quantity of propellant utilized in a full scale rocket motor by burning of the propellant within a chamber of a subscale rocket motor to obtain test data therefrom, the steps of: reducing said quantity of the propellant to a slab dimensioned to fit into the chamber; loading said slab with igniters into the chamber; and heating the slab of the propellant within the chamber to a selected temperature before said burning of the propellant by the igniter to simulate turbulence and pressure environment within the full scale rocket motor.

12. The method of claim 11 wherein said step of reducing the quantity of the propellant comprises: die-cutting the propellant into the slab weighing between two and three ounces.

13. A method of testing rocket propellant to determine ballistic performance of a full scale rocket motor in terms of burn rate of the propellant therein, comprising the steps of: extracting from said propellant a charge adapted to fit into a test chamber of reduced size relative to said full scale rocket motor loading said charge into the test chamber; conditioning the test chamber by heating or cooling thereof to a predetermined temperature under which optimized correlation of burn rate of the charge with the burn rate of the propellant is achieved at all levels of pressure within the test chamber during firing of the charge thereof after said conditioning thereof; measuring said pressure within the test chamber during said firing of the charge; and recording test data on the correlated burning rate of the charge within the test chamber as a function of the pressure measured therein.

* * * * *